(12) United States Patent
Estell

(10) Patent No.: US 6,762,039 B2
(45) Date of Patent: Jul. 13, 2004

(54) BACILLUS SUBTILLIS WITH AN INACTIVATED CYSTEINE PROTEASE-1

(75) Inventor: David A. Estell, San Mateo, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/462,846

(22) PCT Filed: Jul. 14, 1998

(86) PCT No.: PCT/US98/14529

§ 371 (c)(1),
(2), (4) Date: Jan. 13, 2000

(87) PCT Pub. No.: WO99/04016

PCT Pub. Date: Jan. 28, 1999

(65) Prior Publication Data

US 2002/0031807 A1 Mar. 14, 2002

(30) Foreign Application Priority Data

Jul. 15, 1997 (EP) .............................. 97305227

(51) Int. Cl.[7] .............................. C12P 21/04; C12N 1/20
(52) U.S. Cl. .............. 435/69.1; 435/252.5; 435/252.31; 435/71.2
(58) Field of Search .......................... 435/71.2, 252.31, 435/252.5

(56) References Cited

U.S. PATENT DOCUMENTS 5,264,366 A * 11/1993 Ferrari et al. .......... 435/252.31

FOREIGN PATENT DOCUMENTS

WO      WO 89/10976     * 11/1989

OTHER PUBLICATIONS

Broun et al. (1998) Science 282:1315–1317.*
Sloma et al. (1991) J Bacteriol 173(21):6889–6895, Abstract.*

* cited by examiner

Primary Examiner—Rebecca E. Prouty
Assistant Examiner—David J Steadman
(74) Attorney, Agent, or Firm—Genencor International, Inc.

(57) ABSTRACT

The present invention relates to the identification of novel cysteine proteases in Gram-positive microorganisms. The present invention provides the nucleic acid and amino acid sequences for the Bacillus subtilis cysteine proteases CP1, CP2 and CP3. The present invention also provides host cells having a mutation or deletion of part or all of the gene encoding CP1, CP2 or CP3. The present invention also provides host cells further comprising nucleic acid encoding desired heterologous proteins such as enzymes. The present invention also provides a cleaning composition comprising a cysteine protease of the present invention.

7 Claims, 11 Drawing Sheets

```
          10                            30
atgacgactgaaccgttattttt caagcctgttttcaaagaaagaatt
 M  T  T  E  P  L  F  F  K  P  V  F  K  E  R  I 50                      70                      90
tggggcgggaccgctttagctgatttt ggctataccattccgtcacaa
 W  G  G  T  A  L  A  D  F  G  Y  T  I  P  S  Q 110                       130
cgaacaggggagtgctgggcttttgccgcgcatcaaaatggtcaaagc
 R  T  G  E  C  W  A  F  A  A  H  Q  N  G  Q  S 150                       170                       190
gttgttcaaaacggaatgtataaggggttcacgctcagcgaattatgg
 V  V  Q  N  G  M  Y  K  G  F  T  L  S  E  L  W 210                       230
gaacatcacagacatttattcggacagcttgaaggggaccgtttccct
 E  H  H  R  H  L  F  G  Q  L  E  G  D  R  F  P 250                       270                      2
ctgcttacaaaaatattagatgctgaccaggacttatctgttcaggtg
 L  L  T  K  I  L  D  A  D  Q  D  L  S  V  Q  V 90                      310                       330
catccgaatgatgaatatgccaacatacatgaaaacggtgagcttgga
 H  P  N  D  E  Y  A  N  I  H  E  N  G  E  L  G 350                       370
aaaacagaatgctggtacattattgattgccaaaaagatgccgagatt
 K  T  E  C  W  Y  I  I  D  C  Q  K  D  A  E  I 390                       410                       430
atttatggccacaatgcaacaacaaaggaagaactaactaccatgata
 I  Y  G  H  N  A  T  T  K  E  E  L  T  T  M  I 450                       470
gagcgtggagaatgggatgagctcttgcgccgtgtaaaggtaaagccg
 E  R  G  E  W  D  E  L  L  R  R  V  K  V  K  P 490                       510                       5
ggggattttttctatgtgccaagcggtactgttcatgcgattggaaaa
 G  D  F  F  Y  V  P  S  G  T  V  H  A  I  G  K 30                      550                       570
ggaattcttgctttggagacgcagcagaactcagacacaacctacaga
 G  I  L  A  L  E  T  Q  Q  N  S  D  T  T  Y  R
```

FIG._1A

```
                590                           610
ttatatgattatgaccgaaaagatgcagaaggcaagctgcgcgagctt
 L  Y  D  Y  D  R  K  D  A  E  G  K  L  R  E  L 630                 650                       670
catctgaaaaagagcattgaagtgatagaggtcccgtctattccagaa
 H  L  K  K  S  I  E  V  I  E  V  P  S  I  P  E 690                     710
cggcatacagttcaccatgaacaaattgaggatttgcttacaacgaca
 R  H  T  V  H  H  E  Q  I  E  D  L  L  T  T  T 730                   750                          7
ttgattgaatgcgcttacttttcggtggggaaatggaacttatcagga
 L  I  E  C  A  Y  F  S  V  G  K  W  N  L  S  G 70                          790                       810
tcagcaagcttaaagcagcaaaaaccattccttcttatcagtgtgatt
 S  A  S  L  K  Q  Q  K  P  F  L  L  I  S  V  I 830                       850
gaaggggagggccgtatgatctctggtgagtatgtctatcctttcaaa
 E  G  E  G  R  M  I  S  G  E  Y  V  Y  P  F  K 870                       890                     910
aaaggagatcatatgttgctgccttacggtcttggagaatttaaactc
 K  G  D  H  M  L  L  P  Y  G  L  G  E  F  K  L 930
gaaggatatgcagaatgtatcgtctcccatctg
 E  G  Y  A  E  C  I  V  S  H  L
```

FIG._1B

```
                    130       140       150       160       170       180
papa_carpa.p VLNDGDVNIPEYVDWRQKGAVTPVKNQGSQGSCWAFSAVVTIEGIIKIRTGNLNEYSE
             :|       |||:|   : :::::  :|  ::
YJDE         PLFFKPVFKERIWGGTALADFGYTIPSQRTGECWAFAAHQNGQSVVQ---NGMYKGFTL
QE                    10        20        30        40        50        60

190       200       210       220       230       240
papa_carpa.p LLDCDRRSYGCNGG---YPWSALQLVAQYGIHYRNTYPYEGVQRYCRSREKGPYAAKTD
             |:  |::: |   :  ||   |  |   :    ::|| ::|   :|::|   ||
YJDE         LWEHHRHLFGQLEGDRFPLLTKILDADQDLSVQ-VHPND----EYANIHENGELG-KTE
GV                    70        80        90       100       110

250       260       270       280       290
papa_carpa.p RQVQPYNEGALLY---SIANQPVSVVLEAAGKDFQLYR-----GGIFVGPCGNKVDHA
             ::  ||:: ::     : ::: :::::::|    |:|     |:|   |
YJDE         YIIDCQKDAEIIYGHNATTKEELTTMIERGEWDELLRRVVKPGDFFYVPSGT-----
CW                   120       130       140       150       160       170

300       310       320       330       340
papa_carpa.p AVGYGPNYILIKNSWGTGWGENGYIRIKRGTGNSYGVCGLYTSSFYPVKN
             |:|
YJDE         AIGKGILALETQQNSDTTYRLYDYDRKDAEGKLRELHLKKSIEVIEVPSIPERHTVHH
VH                   180       190       200       210       220       230
```

FIG._2

```
59  yjde.pep  MTTEPLFFKPVFKERIWGGTALAD-FGYTIPSQRT GECWAFPAHQNGQSVVQNGMYKG
              ||  |:|: ||||||::|||||   |||| :||:  |||| | |::| |: || |||
 1  PMI       MTQSPIFLTPVFKEKIWGGTALRDRFGYSIPSESTGECWAISAHPKGPSTVANGPYKG
    KT              10        20        30        40        50
                    10        20        30        40        50

19 yjde.pep  LSELWEHHRHLFGQLEGDRFPLLTKILDADQDLSVQVHPNDEYANIHENGELGKTECW
              |  ||| || :|||:||||||||||| |  ||| :|:|:|  | :|| |:|||||||
  1 PMI       LIELWEEHREVFGVEGDRFPLLTKLLDVKEDTSIKVHPDDYYAGENEEGELGKTECW
    YI              70        80        90       100       110
                    60        70        80        90       100       110

79 yjde.pep  IDCQKDAEIIYGHNATTKEELTTMIERGEWDELLKKVKPGDFFYVPSGTVHAIGKG
              |||:|:|||||||:|||:|| ||:|:||| ||||:|||:|||:|||||| ||| ||
  1 PMI       IDCKENAEIIYGHTARSKTELVTMINSGDWEGLLRRIKIKPGDEYYVPSGTLHALCKG
    AL             130       140       150       160       170
                   120       130       140       150       160       170
 80
```

FIG. 3A

```
         180       190       200       210       220       230
yjde.pep ALETQQNSDTTYRLYDYDRKDAEGKLRELHLKKSIEVIEVPSIPERHTVHHEQIEDLL   2
         :|||||:||||:||||  |:::  ||||  |::::  ||:   |:  :  :
PMI      VLETQQNSDATYRVYDYDRLDSNGSPRELHFAKAVNAATVPHVDGYIDESTESRKGIT
         190       200       210       220       230

240       250       260       270       280       290
yjde.pep TLIECAYFSVGKWNLSGSASLKQQKPFLLISVIEGEGRMISGEYVVPFKKGDHMLLPY   2
         |:::  ||||  |::||  ||:::| |  |:: ||  ||||| |  :  :||||||::||
PMI      TFVQGEYFSVYKWDINGEAEMAQDESFLICSVIEGSGLLKYEDKTCPLKKGDHFILPA
         250       260       270       280       290

300       310
yjde.pep GEEKLEGYAECIVSHL   3
         :| ::|  ||||
PMI      PDFTIKGTCTLIVSHI
         310
```

FIG. 3B

```
59  yjde.pep   MTTEPLFFKPVFEKERIWGGTALAD-FGYTIPSQRTGECWAFAAHQNGQSVVQNGMYKG
               |:|||:|||||||::||||| ||||  |  | ||::|||| :|| :|:| |::||
 1  YDHS KT                                  MTHPLFLEPVFEKERLWGGTKLRDAFGYAIPSQKTGECWAVSAHAHGSSSVKNGPLAG
                          10        20        30        40        50

59        70        80        90       100       110

19  yjde.pep   LSELWEHHRHLFGQLEGDRFPLLTKILDADQDLSVQVHPNDEYANIHENGELGKTECW
               |:::|: |   |   |  : ||||:|| ::|||||||:: |:|||:| |||||||
11  YDHS YI    LDQVWKDHPEIFGFPDGKVFPLLVKLLDANMDLSVQVHPDDYAKLHENGDLGKTECW
                          70        80        90       100       110

79       130       140       150       160       170

79  yjde.pep   IDCQKDAEIIYGHNATTKEELTTMIERGEWDELLRRVVKPGDFFYVPSGTVHAIGKG
               |||: ||||| |||:|::|||||  ||:|::||||||:|||:||||||:|| |||
 1  YDHS IL    IDCKDDAELILGHHASTKEEFKQRIESGDWNGLLRRIKIKPGDFFYVPSGTLHALCKG
                         130       140       150       160       170
```

FIG._4A

```
                    180        190       200       210       220       230
39                             ↓  ↓
yjde.pep            ALETQQNSDTTYRLYDYDRKDAEGKLRELHLKKSIEVIEVPSIPERHTVHHEQIEDLL     2
                    :||  ||||||||:|||||| :|: |||:|  |  |  || :  | ::  :::  :
YDHS                VLEIQQNSDTTYRVYDYDRCNDQGQKRTLHIEKAMEVITIPHIDKVHTPEVKEVGNAE
TT                            ↑  ↑
II                  180        190       200       210       220       230

240        250       260       270       280       290
99
yjde.pep            TLIECAYFSVGKWNLSGSASLKQQKPFLLISVIEGEGRMISGEYVYPFKKGDHMLLPY     2
                     : :: ||||  |||:||  :: :|| | | :: ||  | |:|::  | ::::::||
YDHS                VYYQSDYFSVYKWKISGRAAFPSYQTYLLGSVLSGSGRIINNGIQYECNAGSHFILPA
GL                  240        250       260       270       280       290
HF 300        310
yjde.pep            GEFKLEGYAECIVSHL
                    ||| :|| |  :: ||
YDHS                GEFTIEGTCEFMISHP
                    300        310
```

FIG._4B

```
              10                    30
atgacgcatccattattttttagagcctgtctttaaagaaagactatgg
 M  T  H  P  L  F  L  E  P  V  F  K  E  R  L  W 50                 70                   90
ggagggacgaagcttcgtgacgcttttggctacgcaatacccctcacaa
 G  G  T  K  L  R  D  A  F  G  Y  A  I  P  S  Q 110                  130
aaaacaggtgagtgctgggccgtttctgcacatgcccatggctcgtcg
 K  T  G  E  C  W  A  V  S  A  H  A  H  G  S  S 150                 170                  190
tctgtaaaaaatggcccgctggcaggaaagacacttgatcaagtatgg
 S  V  K  N  G  P  L  A  G  K  T  L  D  Q  V  W 210                   230
aaagatcatccagagatattcgggtttccggatggtaaggtgtttccg
 K  D  H  P  E  I  F  G  F  P  D  G  K  V  F  P 250                   270                 2
ctgctggtaaagctgctggacgccaatatggatctctccgtgcaagtc
 L  L  V  K  L  L  D  A  N  M  D  L  S  V  Q  V 90                  310                   330
catcctgatgatgattatgcaaaactgcacgaaaatggcgaccttggt
 H  P  D  D  D  Y  A  K  L  H  E  N  G  D  L  G 350                   370
aaaacggagtgctggtatatcattgattgcaaagatgacgccgaacta
 K  T  E  C  W  Y  I  I  D  C  K  D  D  A  E  L 390                   410                   430
attttgggacatcatgcaagcacaaaggaagagttcaaacaacgaata
 I  L  G  H  H  A  S  T  K  E  E  F  K  Q  R  I 450                    470
gaaagcggtgattggaacgggctgctgaggcgaatcaaaatcaagcca
 E  S  G  D  W  N  G  L  L  R  R  I  K  I  K  P 490                    510            5
ggagatttcttttatgtgccaagcggtacactccatgctttatgtaag
 G  D  F  F  Y  V  P  S  G  T  L  H  A  L  C  K 30                  550                   570
ggaacccttgtccttgaaatccagcaaaactctgatacaacatatcgc
 G  T  L  V  L  E  I  Q  Q  N  S  D  T  T  Y  R
```

*FIG._5A*

```
             590                        610
gtatacgattatgaccgctgtaatgaccagggccaaaaaagaactctt
 V   Y   D   Y   D   R   C   N   D   Q   G   Q   K   R   T   L 630           650                        670
catatagaaaaagccatggaagtcataacgataccgcatatcgataaa
 H   I   E   K   A   M   E   V   I   T   I   P   H   I   D   K 690                        710
gtgcatacaccggaagtaaaagaagttggtaacgctgagatcattgtt
 V   H   T   P   E   V   K   E   V   G   N   A   E   I   I   V 730                        750                   7
tatgtgcaatcagattatttctcagtgtacaaatggaagattagcggc
 Y   V   Q   S   D   Y   F   S   V   Y   K   W   K   I   S   G 70                       790                        810
cgagctgcttttccttcatatcaaacctatttgctggggagtgttctg
 R   A   A   F   P   S   Y   Q   T   Y   L   L   G   S   V   L 830                        850
agcggatcaggacgaatcataaataatggtattcagtatgaatgcaat
 S   G   S   G   R   I   I   N   N   G   I   Q   Y   E   C   N 870                       890                        910
gcaggctcacactttattctgcctgcgcattttggagaatttacaata
 A   G   S   H   F   I   L   P   A   H   F   G   E   F   T   I 930
gaaggaacatgtgaattcatgatatctcatcct
 E   G   T   C   E   F   M   I   S   H   P
```

*FIG._5B*

```
                10                      30
  atgacgcaatcaccgattttctaacgcctgtgtttaaagaaaaaatc
   M  T  Q  S  P  I  F  L  T  P  V  F  K  E  K  I 50                  70                   90
  tggggcggaaccgctttacgagatagatttggatacagtattccttca
   W  G  G  T  A  L  R  D  R  F  G  Y  S  I  P  S 110                     130
  gaatcaacggggggaatgctgggccatttccgctcatccaaaaggaccg
   E  S  T  G  E  C  W  A  I  S  A  H  P  K  G  P 150                 170                  190
  agcactgttgcaaatggcccgtataaggaaagacattgatcgagctt
   S  T  V  A  N  G  P  Y  K  G  K  T  L  I  E  L 210                    230
  tggggaagagcaccgtgaagtattcggcggcgtagagggggatcggttt
   W  E  E  H  R  E  V  F  G  G  V  E  G  D  R  F 250                    270              2
  ccgcttctgacaaagctgctggatgtgaaggaagatacgtcaattaaa
   P  L  L  T  K  L  L  D  V  K  E  D  T  S  I  K 90                  310                   330
  gttcaccctgatgattactatgccggagaaaacgaagagggagaactc
   V  H  P  D  D  Y  Y  A  G  E  N  E  E  G  E  L 350                    370
  ggcaagacggaatgctggtacattatcgactgtaaggaaaacgcagaa
   G  K  T  E  C  W  Y  I  I  D  C  K  E  N  A  E 390                   410                  430
  atcatttacgggcatacggcccgctcaaaaaccgaacttgtcacaatg
   I  I  Y  G  H  T  A  R  S  K  T  E  L  V  T  M 450                   470
  atcaacagcggtgactgggagggcctgctgcgaagaatcaaaattaaa
   I  N  S  G  D  W  E  G  L  L  R  R  I  K  I  K 490                    510              5
  ccgggtgatttctattatgtgccgagcggaacgctgcacgcattgtgc
   P  G  D  F  Y  Y  V  P  S  G  T  L  H  A  L  C 30                  550                   570
  aagggggcccttgttttagagactcagcaaaattcagatgccacatac
   K  G  A  L  V  L  E  T  Q  Q  N  S  D  A  T  Y
```

FIG._6A

```
                590                         610
      cgggtgtacgattatgaccgtcttgatagcaacggaagtccgagagag
       R  V  Y  D  Y  D  R  L  D  S  N  G  S  P  R  E 630                       650                     670
      cttcattttgccaaagcggtcaatgccgccacggttccccatgtggac
       L  H  F  A  K  A  V  N  A  A  T  V  P  H  V  D 690                       710
      gggtatatagatgaatcgacagaatcaagaaaaggaataaccattaaa
       G  Y  I  D  E  S  T  E  S  R  K  G  I  T  I  K 730                          750                    7
      acatttgtccaaggggaatatttttcggtttataaatgggacatcaat
       T  F  V  Q  G  E  Y  F  S  V  Y  K  W  D  I  N 70                         790                      810
      ggcgaagctgaaatggctcaggatgaatcctttctgatttgcagcgtg
       G  E  A  E  M  A  Q  D  E  S  F  L  I  C  S  V 830                       850
      atagaaggaagcggtttgctcaagtatgaggacaaaacatgtccgctc
       I  E  G  S  G  L  L  K  Y  E  D  K  T  C  P  L 870                        890                      910
      aaaaaaggtgatcactttattttgccggctcaaatgcccgattttacg
       K  K  G  D  H  F  I  L  P  A  Q  M  P  D  F  T 930
      ataaaaggaacttgtaccecttatcgtgtctcatatt
       I  K  G  T  C  T  L  I  V  S  H  I
```

BACILLUS SUBTILLIS WITH AN INACTIVATED CYSTEINE PROTEASE-1

FIELD OF THE INVENTION

The present invention relates to cysteine proteases derived from gram-positive microorganisms. The present invention provides nucleic acid and amino acid sequences of cysteine protease 1, 2 and 3 identified in Bacillus. The present invention also provides methods for the production of cysteine protease 1, 2 and 3 in host cells as well as the production of heterologous proteins in a host cell having a mutation or deletion of part or all of at least one of the cysteine proteases of the present invention.

BACKGROUND OF THE INVENTION

Gram-positive microorganisms, such as members of the group Bacillus, have been used for large-scale industrial fermentation due, in part, to their ability to secrete their fermentation products into the culture media. In gram-positive bacteria, secreted proteins are exported across a cell membrane and a cell wall, and then are subsequently released into the external media usually maintaining their native conformation.

Various gram-positive microorganisms are known to secrete extracellular and/or intracellular protease at some stage in their life cycles. Many proteases are produced in large quantities for industrial purposes. A negative aspect of the presence of proteases in gram-positive organisms is their contribution to the overall degradation of secreted heterologous or foreign proteins.

The classification of proteases found in microorganisms is based on their catalytic mechanism which results in four groups: the serine proteases; metalloproteases; cysteine proteases; and aspartic proteases. These categories can be distinguished by their sensitivity to various inhibitors. For example, the serine proteases are inhibited by phenylmethylsulfonylfluoride (PMSF) and diisopropylfluorophosphate (DIFP); the metalloproteases by chelating agents; the cysteine enzymes by iodoacetamide and heavy metals and the aspartic proteases by pepstatin. The serine proteases have alkaline pH optima, the metalloproteases are optimally active around neutrality, and the cysteine and aspartic enzymes have acidic pH optima (*Biotechnology Handbooks, Bacillus*. vol. 2, edited by Harwood, 1989 Plenum Press, New York).

The activity of cysteine protease depends on a catalytic dyad of cysteine and histidine with the order differing among families. The best known family of cysteine proteases is that of papain having catalytic residues Cys-25 and His-159. Cysteine proteases of the papain family catalyze the hydrolysis of peptide, amide, ester, thiol ester and thiono ester bonds. Naturally occurring inhibitors of cysteine proteases of the papain family are those of the cystatin family (Methods in Enzymology, vol. 244, Academic Press, Inc. 1994).

SUMMARY OF THE INVENTION

The present invention relates to the unexpected and surprising discovery of three heretofore unknown or unrecognized cysteine proteases found in *Bacillus subtilis*, designated herein as CP1, CP2 and CP3, having the nucleic acid and amino acid as shown in FIGS. 1A–1B, FIGS. 5A–5B and 6A–6B, respectively. The present invention is based in part, upon the presence of the characteristic cysteine protease amino acid motif GXCWAF found in uncharacterised translated genomic nucleic acid sequences of *Bacillus subtilis*. The present invention is also based in part upon the structural relatedness that CP1 has with the cysteine protease papain specifically with respect to the location of the catalytic histidine/alanine and asparagine/serine residues and the structural relatedness that CP1 has with CP2 and CP3.

The present invention provides isolated polynucleotide and amino acid sequences for CP1, CP2 and CP3. Due to the degeneracy of the genetic code, the present invention encompasses any nucleic acid sequence that encodes the CP1, CP2 and CP3 amino acid sequence shown in the Figures.

The present invention encompasses amino acid variations of *B.subtilis* CP1, CP2 and CP3 amino acids disclosed herein that have proteolytic activity. *B. subtilis* CP1, CP2 and CP3, as well as proteolytically active amino acid variations thereof, have application in cleaning compositions. In one aspect of the present invention, CP1, CP2 or CP3 obtainable from a gram-positive microorganism is produced on an industrial fermentation scale in a microbial host expression system. In another aspect, isolated and purified recombinant CP1, CP2 or CP3 obtainable from a gram-positive microorganism is used in compositions of matter intended for cleaning purposes, such as detergents. Accordingly, the present invention provides a cleaning composition comprising at least one of CP1, CP2 and CP3 obtainable from a gram-positive microorganism. The cysteine protease may be used alone in the cleaning composition or in combination with other enzymes and/or mediators or enhancers.

The production of desired heterologous proteins or polypeptides in gram-positive microorganisms may be hindered by the presence of one or more proteases which degrade the produced heterologous protein or polypeptide. Therefore, the present invention also encompasses gram-positive microorganism having a mutation or deletion of part or all of the gene encoding CP1 and/or CP2 and/or CP3, which results in the inactivation of the CP1 and/or CP2 and/or CP3 proteolytic activity, either alone or in combination with deletions or mutations in other proteases, such as apr, npr, epr, mpr for example, or other proteases known to those of skill in the art. In one embodiment of the present invention, the gram-positive organism is a member of the genus Bacillus. In another embodiment, the Bacillus is *Bacillus subtilis*.

In another aspect, the gram-positive microorganism host having one or more deletions or mutations in a cysteine protease of the present invention is further genetically engineered to produce a desired protein. In one embodiment of the present invention, the desired protein is heterologous to the gram-positive host cell. In another embodiment, the desired protein is homologous to the host cell. The present invention encompasses a gram-positive host cell having a deletion or interruption of the naturally occurring nucleic acid encoding the homologous protein, such as a protease, and having nucleic acid encoding the homologous protein or a variant thereof re-introduced in a recombinant form. In another embodiment, the host cell produces the homologous protein. Accordingly, the present invention also provides methods and expression systems for reducing degradation of heterologous or homologous proteins produced in gram-positive microorganisms comprising the steps of obtaining a Bacillus host cell comprising nucleic acid encoding said heterologous protein wherein said host cell contains a mutation or deletion in at least one of the genes encoding cysteine protease 1, cysteine protease 2 and cysteine protease 3; and growing said Bacillus host cell under conditions suitable for the expression of said heterologous protein. The gram-positive microorganism may be normally sporulating or non-sporulating.

The present invention provides methods for detecting gram positive microorganism homologs of *B. subtilis* CP1, CP2 and CP3 that comprises hybridizing part or all of the nucleic acid encoding *B. subtilis* CP1, CP2 and CP3 with nucleic acid derived from gram-positive organisms, either of genomic or cDNA origin.

BRIEF DESCRIPTION OF THE DRAWINGS

FIGS. 1A–1B shows the DNA (SEQ ID NO:1) and amino acid sequence for CP1 (YJDE) (SEQ ID NO:2).

FIG. 2 shows an amino acid alignment with papain (SEQ ID NO:3) (accession number papa_carpa p) with the cysteine protease CP1, designated YJDE. For FIGS. 2, 3 and 4, the motif GXCWAF has been marked along with the catalytic cysteine and the conserved catalytic histidine/alanine and asparagine/serine residues.

FIG. 3 shows amino acid alignment of CP1 (YJDE) (SEQ ID NO:2) with CP3 (PMI) (SEQ ID NO:5).

FIG. 4 shows the amino acid alignment of CP1 (YJDE) (SEQ ID NO:2) with CP2 (YdhS).

FIGS. 5A–5B shows the amino acid (SEQ ID NO:6) and nucleic acid sequence for CP2 (YdhS) (SEQ ID NO:7).

FIGS. 6A–6B shows the amino acid (SEQ ID NO:4) and nucleic acid sequence for CP3 (PMI) (SEQ ID NO:5).

DETAILED DESCRIPTION OF THE PREFERRED EMBODIMENTS

Definitions

As used herein, the genus Bacillus includes all members known to those of skill in the art, including but not limited to *B. subtilis, B. licheniformis, B. lentus, B. brevis, B. stearothermophilus, B. alkalophilus, B. amyloliquefaciens, B. coagulans, B. ciculans, B. lautus* and *B. thuringiensis.*

The present invention relates to novel CP1, CP2 and CP3 from gram positive organisms. In a preferred embodiment, the gram-positive organisms is a Bacillus. In another preferred embodiment, the gram-positive organism is *Bacillus subtilis.* As used herein, "*B.subtilis* CP1, CP2 or CP3 " refers to the amino acid sequences shown in Figures. FIGS. 1A–1B show the amino acid and nucleic acid seqeunce for CP1 (YJDE); FIGS. 5A–5B show the amino acid and nucleic acid sequence for CP2 (YDHS); and FIGS. 6A–6B show the amino acid and nucleic acid sequences for CP3 (PMI). The present invention encompasses amino acid variations of the amino acid sequences disclosed in FIGS. 1A–1B and 5A–5B and 6A–6B that have proteolytic activity. Such proteolytic amino acid variants can be used in cleaning compositions.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof. A "polynucleotide homolog" as used herein refers to a gram-positive microorganism polynucleotide that has at least 80%, at least 90% and at least 95% identity to *B.subtilis* CP1, CP2 or CP3, or which is capable of hybridizing to *B.subtilis* CP1, CP2 or CP3 under conditions of high stringency and which encodes an amino acid sequence having cysteine protease activity.

The terms "isolated" or "purified" as used herein refer to a nucleic acid or amino acid that is removed from at least one component with which it is naturally associated.

As used herein, the term "heterologous protein" refers to a protein or polypeptide that does not naturally occur in a gram-positive host cell Examples of heterologous proteins include enzymes such as hydrolases including proteases, cellulases, amylases, carbohydrases, and lipases; isomerases such as racemases, epimerases, tautomerases, or mutases; transferases, kinases and phophatases. The heterologous gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrases such as amylases and glucoamylases, cellulases, oxidases and lipases. The gene of interest may be a naturally occurring gene, a mutated gene or a synthetic gene.

The term "homologous protein" refers to a protein or polypeptide native or naturally occurring in a gram-positive host cell. The invention includes host cells producing the homologous protein via recombinant DNA technology. The present invention encompasses a gram-positive host cell having a deletion or interruption of naturally occurring nucleic acid encoding the homologous protein, such as a protease, and having nucleic acid encoding the homologous protein, or a variant thereof, re-introduced in a recombinant form. In another embodiment, the host cell produces the homologous protein.

As used herein, the term "overexpressing" when refering to the production of a protein in a host cell means that the protein is produced in greater amounts than its production in its naturally occurring environment.

As used herein, the phrase "proteolytic activity" refers to a protein that is able to hydrolyze a peptide bond. Enzymes having proteolytic activity are described in Enzyme Nomenclature, 1992, edited Webb Academic Press, Inc.

DETAILED DESCRIPTION OF THE PREFERRED EMBODIMENTS

The unexpected discovery of the cysteine proteases CP1, CP2 and CP3 in *B.subtilis* provides a basis for producing host cells, expression methods and systems which can be used to prevent the degradation of recombinantly produced heterologous proteins. In a preferred embodiment, the host cell is a gram-positive host cell that has a deletion or mutation in the naturally occurring cysteine protease said mutation resulting in deletion or inactivation of the production by the host cell of the proteolytic cysteine protease gene product. The host cell may additionally be genetically engineered to produced a desired protein or polypeptide.

It may also be desired to genetically engineer host cells of any type to produce a gram-positive cysteine protease. Such host cells are used in large scale fermentation to produce large quantities of the cysteine protease which may be isolated or purified and used in cleaning products, such as detergents.

I. Cysteine Protease Sequences

The CP1, CP2 and CP3 polynucleotides having the sequences as shown in FIGS. 1A–1B, 5A–5B and 6A–6B, respectively, encode the *Bacillus subtilis* cysteine proteases CP1, CP2 and CP3. As will be understood by the skilled artisan, due to the degeneracy of the genetic code, a variety of polynucleotides can encode the *Bacillus subtilis* CP1, CP2 and CP3. The present invention encompasses all such polynucleotides.

The present invention encompasses CP1, CP2 and CP3 polynucleotide homologs encoding gram-positive microorganism cysteine proteases CP1, CP2 and CP3, respectively, which have at least 80%, or at least 90% or at least 95% identity to B.subtilis CP1, CP2 and CP3 as long as the homolog encodes a protein that has proteolytic activity.

Gram-positive polynucleotide homologs of B.subtilis CP1, CP2 or CP3 may be obtained by standard procedures known in the art from, for example, cloned DNA (e.g., a DNA "library") genomic DNA libraries, by chemical synthesis once identified, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) A preferred source is from genomic DNA. Nucleic acid sequences derived from genomic DNA may contain regulatory regions in addition to coding regions. Whatever the source, the isolated CP1, CP2 or CP3 gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the CP1, CP2 or CP3 may be accomplished in a number of ways. For example, a B.subtilis CP1, CP2 or CP3 gene of the present invention or its specific RNA, or a fragment thereof, such as a probe or primer, may be isolated and labeled and then used in hybridization assays to detect a gram-positive CP1, CP2 or CP3 gene. (Benton, W. and Davis, R., 1977, Science 196:180; Grunstein, M. And Hogness, D., 1975, Proc. Natl. Acad. Sci. USA 72:3961). Those DNA fragments sharing substantial sequence similarity to the probe will hybridize under stringent conditions.

Accordingly, the present invention provides a method for the detection of gram-positive CP1, CP2 and CP3 polynucleotide homologs which comprises hybridizing part or all of a nucleic acid sequence of B. subtilis CP1, CP2 and CP3 with gram-positive microorganism nucleic acid of either genomic or cDNA origin.

Also included within the scope of the present invention are gram-positive microorganism polynucleotide sequences that are capable of hybridizing to the nucleotide sequence of B.subtilis CP1, CP2 or CP3 under conditions of intermediate to maximal stringency. Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The term "hybridization" as used herein shall include "the process by which a strand of nucleic acid joins with a complementary strand through base pairing" (Coombs J (1994) Dictionary of Biotechnology, Stockton Press, New York N.Y.).

The process of amplification as carried out in polymerase chain reaction (PCR) technologies is described in Dieffenbach C W and G S Dveksler (1995, PCR Primer, a Laboratory Manual, Cold Spring Harbor Press, Plainview N.Y.). A nucleic acid sequence of at least about 10 nucleotides and as many as about 60 nucleotides from B. subtilis CP1, CP2 or CP3 preferably about 12 to 30 nucleotides, and more preferably about 20–25 nucleotides can be used as a probe or PCR primer.

The B.subtilis amino acid sequences CP1, CP2 and CP3 (shown in FIGS. 2, 4 and 3, respectively) were identified via a FASTA search of Bacillus subtilis genomic nucleic acid sequences. B. subtilis CP1 (YJDE) was identified by its structural homology to the cysteine protease papain having the sequence designated "papa_carpa.p". As shown in FIG. 2, YJDE has the motif GXCWAF as well as the conserved catalytic residues His/Ala and Asn/Ser. CP2 (YdHS) and CP3 (PMI) were identified upon their structural homology to CP1 (YJDE). The presence of GXCWAF as well as residues His/Ala and Asn/Ser is noted in FIGS. 3 and 4. CP3 (PMI) was previously characterized as a possible phosphomannose isomerase, (Noramata). There has been no previous characterization of CP3 as a cysteine protease.

II. Expression Systems

The present invention provides host cells, expression methods and systems for the enhanced production and secretion of desired heterologous or homologous proteins in gram-positive microorganisms. In one embodiment, a host cell is genetically engineered to have a deletion or mutation in the gene encoding a gram-positive CP1, CP2 or CP3 such that the respective activity is deleted. In another embodiment of the present invention, a gram-positive microorganism is genetically engineered to produce a cysteine protease of the present invention.

Inactivation of a Gram-Positive Cysteine Protease in a Host Cell

Producing an expression host cell incapable of producing the naturally occurring cysteine protease necessitates the replacement and/or inactivation of the naturally occurring gene from the genome of the host cell. In a preferred embodiment, the mutation is a non-reverting mutation.

One method for mutating nucleic acid encoding a gram-positive cysteine protease is to clone the nucleic acid or part thereof, modify the nucleic acid by site directed mutagenesis and reintroduce the mutated nucleic acid into the cell on a plasmid. By homologous recombination, the mutated gene may be introduced into the chromosome. In the parent host cell, the result is that the naturally occurring nucleic acid and the mutated nucleic acid are located in tandem on the chromosome. After a second recombination, the modified sequence is left in the chromosome having thereby effectively introduced the mutation into the chromosomal gene for progeny of the parent host cell.

Another method for inactivating the cysteine protease proteolytic activity is through deleting the chromosomal gene copy. In a preferred embodiment, the entire gene is deleted, the deletion occurring in such as way as to make reversion impossible. In another preferred embodiment, a partial deletion is produced, provided that the nucleic acid sequence left in the chromosome is too short for homologous recombination with a plasmid encoded cysteine protease gene. In another preferred embodiment, nucleic acid encoding the catalytic amino acid residues are deleted.

Deletion of the naturally occurring gram-positive microorganism cysteine protease can be carried out as follows. A cysteine protease gene including its 5' and 3' regions is isolated and inserted into a cloning vector. The coding region of the cysteine protease gene is deleted form the vector in vitro, leaving behind a sufficient amount of the 5' and 3' flanking sequences to provide for homologous recombination with the naturally occurring gene in the parent host cell. The vector is then transformed into the gram-positive host cell. The vector integrates into the chromosome via homologous recombination in the flanking regions. This method leads to a gram-positive strain in which the protease gene has been deleted.

The vector used in an integration method is preferably a plasmid. A selectable marker may be included to allow for ease of identification of desired recombinant microorganisms. Additionally, as will be appreciated by one of skill in the art, the vector is preferably one which can be selectively integrated into the chromosome. This can be achieved by introducing an inducible origin of replication, for example, a temperature sensitive origin into the plasmid. By growing the transformants at a temperature to which the origin of replication is sensitive, the replication function of the plasmid is inactivated, thereby providing a means for selection of chromosomal integrants. Integrants may be selected for growth at high temperatures in the presence of the selectable marker, such as an antibiotic. Integration mechanisms are described in WO 88/06623.

Integration by the Campbell-type mechanism can take place in the 5' flanking region of the protease gene, resulting in a protease positive strain carrying the entire plasmid vector in the chromosome in the cysteine protease locus. Since illegitimate recombination will give different results it will be necessary to determine whether the complete gene has been deleted, such as through nucleic acid sequencing or restriction maps.

Another method of inactivating the naturally occurring cysteine protease gene is to mutagenize the chromosomal gene copy by transforming a gram-positive microorganism with oligonucleotides which are mutagenic. Alternatively, the chromosomal cysteine protease gene can be replaced with a mutant gene by homologous recombination.

The present invention encompasses host cells having deletions or mutations of a cysteine protease of the present invention as well as additional protease deletions or mutations, such as deletions or mutations in apr, npr, epr, mpr and others known to those of skill in the art. U.S. Pat. No. 5,264,366 discloses Bacillus host cells having a deletion of apr and npr; U.S. Pat. No. 5,585,253 discloses Bacillus host cells having a deletion of epr; Margot et al., 1996, Microbiology 142: 3437–3444 disclose host cells having a deletion in wpr and EP patent 0369817 discloses Bacillus host cells having a deletion of mpr.

One assay for the detection of mutants involves growing the Bacillus host cell on medium containing a protease substrate and measuring the appearance or lack thereof, of a zone of clearing or halo around the colonies. Host cells which have an inactive protease will exhibit little or no halo around the colonies.

III. Production of Cysteine Protease

For production of cysteine protease in a host cell, an expression vector comprising at least one copy of nucleic acid encoding a gram-positive microorganism CP1, CP2 or CP3, and preferably comprising multiple copies, is transformed into the host cell under conditions suitable for expression of the cysteine protease. In accordance with the present invention, polynucleotides which encode a gram-positive microorganism CP1, CP2 or CP3, or fragments thereof, or fusion proteins or polynucleotide homolog sequences that encode amino acid variants of *B.subtilis* CP1, CP2 or CP3, may be used to generate recombinant DNA molecules that direct their expression in host cells. In a preferred embodiment, the gram-positive host cell belongs to the genus Bacillus. In another preferred embodiment, the gram positive host cell is *B. subtilis*.

As will be understood by those of skill in the art, it may be advantageous to produce polynucleotide sequences possessing non-naturally occurring codons. Codons preferred by a particular gram-positive host cell (Murray E et al (1989) Nuc Acids Res 17:477–508) can be selected, for example, to increase the rate of expression or to produce recombinant RNA transcripts having desirable properties, such as a longer half-life, than transcripts produced from naturally occurring sequence.

Altered CP1, CP2 or CP3 polynucleotide sequences which may be used in accordance with the invention include deletions, insertions or substitutions of different nucleotide residues resulting in a polynucleotide that encodes the same or a functionally equivalent CP1, CP2 or CP3 homolog, respectively. As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring CP1, CP3 or CP3.

As used herein "substitution" results from the replacement of one or more nucleotides or amino acids by different nucleotides or amino acids, respectively.

The encoded protein may also show deletions, insertions or substitutions of amino acid residues which produce a silent change and result in a functionally CP1, CP2 or CP3 variant. Deliberate amino acid substitutions may be made on the basis of similarity in polarity, charge, solubility, hydrophobicity, hydrophilicity, and/or the amphipathic nature of the residues as long as the variant retains the ability to modulate secretion. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

The CP1, CP2 or CP3 polynucleotides of the present invention may be engineered in order to modify the cloning, processing and/or expression of the gene product. For example, mutations may be introduced using techniques which are well known in the art, eg, site-directed mutagenesis to insert new restriction sites, to alter glycosylation patterns or to change codon preference, for example.

In one embodiment of the present invention, a gram-positive microorganism CP1, CP2 or CP3 polynucleotide may be ligated to a heterologous sequence to encode a fusion protein. A fusion protein may also be engineered to contain a cleavage site located between the cysteine protease nucleotide sequence and the heterologous protein sequence, so that the cysteine protease may be cleaved and purified away from the heterologous moiety.

IV. Vector Sequences

Expression vectors used in expressing the cysteine proteases of the present invention in gram-positive microorganisms comprise at least one promoter associated with a cysteine protease selected from the group consisting of CP1, CP2 and CP3, which promoter is functional in the host cell. In one embodiment of the present invention, the promoter is the wild-type promoter for the selected cysteine protease and in another embodiment of the present invention, the promoter is heterologous to the cysteine protease, but still functional in the host cell. In one preferred embodiment of the present invention, nucleic acid encoding the cysteine protease is stably integrated into the microorganism genome.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the gram-positive host which allows for ease of selection of those hosts containing the vector. Examples of such selectable markers include but are not limited to antibiotics, such as, erythromycin, actinomycin, chloramphenicol and tetracycline.

V. Transformation

A variety of host cells can be used for the production of CP1, CP2 and CP3 including bacterial, fungal, mammalian and insects cells. General transformation procedures are taught in Current Protocols In Molecular Biology (vol.1, edited by Ausubel et al., John Wiley & Sons, Inc. 1987, Chapter 9) and include calcium phosphate methods, transformation using DEAE-Dextran and electroporation. Plant transformation methods are taught in Rodriquez (WO 95/14099, published May 26, 1995).

In a preferred embodiment, the host cell is a gram-positive microorganism and in another preferred embodiment, the host cell is Bacillus. In one embodiment of the present invention, nucleic acid encoding one or more cysteine protease(s) of the present invention is introduced into a host cell via an expression vector capable of replicating within the Bacillus host cell. Suitable replicating plasmids for Bacillus are described in Molecular Biological Methods for Bacillus, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, nucleic acid encoding a cysteine protease(s) of the present invention is stably integrated into the microorganism genome. Preferred host cells are gram-positive host cells. Another preferred host is Bacillus. Another preferred host is *Bacillus subtilis*. Several strategies have been described in the literature for the direct cloning of DNA in Bacillus. Plasmid marker rescue transformation involves the uptake of a donor plasmid by competent cells carrying a partially homologous resident plasmid (Contente et al., Plasmid 2:555–571 (1979); Haima et al., Mol. Gen. Genet. 223:185–191 (1990); Weinrauch et al., J. Bacteriol. 154(3):1077–1087 (1983); and Weinrauch et al., J. Bacteriol. 169(3):1205–1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979) Mol. Gen. Genet 168:111–115; for *B.megaterium* in Vorobjeva et al., (1980) FEMS Microbiol. Letters 7:261–263; for *B. amyloliquefaciens* in Smith et al., (1986) Appl. and Env. Microbiol. 51:634; for *B.thuringiensis* in Fisher et al., (1981) Arch. Microbiol. 139:213–217; for *B.sphaericus* in McDonald (1984) J. Gen. Microbiol. 130:203; and *B.larvae* in Bakhiet et al., (1985) 49:577. Mann et al., (1986, Current Microbiol. 13:131–135) report on transformation of Bacillus protoplasts and Holubova, (1985) Folia Microbiol. 30:97) disclose methods for introducing DNA into protoplasts using DNA containing liposomes.

VI. Identification of Transformants

Whether a host cell has been transformed with a mutated or a naturally occurring gene encoding a gram-positive CP1, CP2 or CP3, detection of the presence/absence of marker gene expression can suggests whether the gene of interest is present However, its expression should be confirmed. For example, if the nucleic acid encoding a cysteine protease is inserted within a marker gene sequence, recombinant cells containing the insert can be identified by the absence of marker gene function. Alternatively, a marker gene can be placed in tandem with nucleic acid encoding the cysteine protease under the control of a single promoter. Expression of the marker gene in response to induction or selection usually indicates expression of the cysteine protease as well.

Alternatively, host cells which contain the coding sequence for a cysteine protease and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the cysteine polynucleotide sequence can be detected by DNA-DNA or DNA-RNA hybridization or amplification using probes, portions or fragments of *B.subtilis* CP1, CP2 or CP3.

VII. Assay of Protease Activity

There are various assays known to those of skill in the art for detecting and measuring protease activity. There are assays based upon the release of acid-soluble peptides from casein or hemoglobin measured as absorbance at 280 nm or colorimetrically using the Folin method (Bergmeyer, et al., 1984, Methods of Enzymatic Analysis vol. 5, Peptidases, Proteinases and their Inhibitors, Verlag Chemie, Weinheim). Other assays involve the solubilization of chromogenic substrates (Ward, 1983, Proteinases, in Microbial Enzymes and Biotechnology (W. M. Fogarty, ed.), Applied Science, London, pp. 251–317).

VIII. Secretion of Recombinant Proteins

Means for determining the levels of secretion of a heterologous or homologous protein in a gram-positive host cell and detecting secreted proteins include, using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton R et al (1990, Serological Methods, a Laboratory Manual, APS Press, St Paul Minn.) and Maddox Del. et al (1983, J Exp Med 158:1211).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 and incorporated herein by reference.

IX. Purification of Proteins

Gram positive host cells transformed with polynucleotide sequences encoding heterologous or homologous protein may be cultured under conditions suitable for the expression and recovery of the encoded protein from cell culture. The protein produced by a recombinant gram-positive host cell comprising a mutation or deletion of the cysteine protease activity will be secreted into the culture media. Other recombinant constructions may join the heterologous or homologous polynucleotide sequences to nucleotide sequence encoding a polypeptide domain which will facilitate purification of soluble proteins (Kroll D J et al (1993) DNA Cell Biol 12:441–53).

Such purification facilitating domains include, but are not limited to, metal chelating peptides such as histidine-tryptophan modules that allow purification on immobilized metals (Porath J (1992) Protein Expr Purif 3:263–281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification.

X. Uses of The Present Invention CP1, CP2 and CP3 and Genetically Engineered Host Cells The present invention provides genetically engineered host cells comprising preferably non-revertable mutations or deletions in the naturally occurring gene encoding CP1, CP2 or CP3 such that the proteolytic activity is diminished or deleted altogether. The host cell may contain additional protease deletions, such as deletions of the mature subtilisn protease and/or mature neutral protease disclosed in U.S. Pat. No. 5,264,366.

In a preferred embodiment, the host cell is further genetically engineered to produce a desired protein or polypeptide. In a preferred embodiment the host cell is a Bacillus. In another preferred embodiment, the host cell is a *Bacillus subtilis*.

In an alternative embodiment, a host cell is genetically engineered to produce a gram-positive CP1, CP2 or CP3. In a preferred embodiment, the host cell is grown under large scale fermentation conditions, the CP1, CP2 or CP3 is isolated and/or purified and used in cleaning compositions such as detergents. Detergent formulations are disclosed in WO 95/10615. A cysteine protease of the present invention can be useful in formulating various cleaning compositions. A number of known compounds are suitable surfactants useful in compositions comprising the cysteine protease of the invention. These include nonionic, anionic, cationic, anionic or zwitterionic detergents, as disclosed in U.S. Pat. Nos. 4,404,128 and 4,261,868. A suitable detergent formulation is that described in Example 7 of U.S. Pat. No. 5,204,015. The art is familiar with the different formulations which can be used as cleaning compositions. In addition, a cysteine protease of the present invention can be used, for example, in bar or liquid soap applications, dishcare formulations, contact lens cleaning solutions or products, peptide hydrolysis, waste treatment, textile applications, as fusion-cleavage enzymes in protein production, etc. A cysteine protease may provide enhanced performance in a detergent composition (as compared to another detergent protease). As used herein, enhanced performance in a detergent is defined as increasing cleaning of certain enzyme sensitive stains such as grass or blood, as determined by usual evaluation after a standard wash cycle.

A cysteine protease of the present invention can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of a cysteine protease to conventional cleaning compositions does not create any special use limitation. In other words, any temperature and pH suitable for the detergent is also suitable for the present compositions as long as the pH is within the above range, and the temperature is below the described cysteine protease denaturing temperature. In addition, a cysteine protease can be used in a cleaning composition without detergents, again either alone or in combination with builders and stabilizers.

One aspect of the invention is a composition for the treatment of a textile that includes a cysteine protease of the present invention. The composition can be used to treat for example silk or wool as described in publications such as RD 216,034; EP 134,267; U.S. Pat No. 4,533,359; and EP 344,259.

Proteases can be included in animal feed such as part of animal feed additives as described in, for example, U.S. Pat. Nos. 5,612,055; 5,314,692; and 5,147,642.

CP1, CP2 and CP3 Polynucleotides

A *B.subtilis* polynucleotide, or any part thereof, provides the basis for detecting the presence of gram-positive microorganism polynucleotide homologs through hybridization techniques and PCR technology.

Accordingly, one aspect of the present invention is to provide for nucleic acid hybridization and PCR probes which can be used to detect polynucleotide sequences, including genomic and cDNA sequences, encoding gram-positive CP1, CP2 or CP3 or portions thereof.

The manner and method of carrying out the present invention may be more fully understood by those of skill in the art by reference to the following examples, which examples are not intended in any manner to limit the scope of the present invention or of the claims directed thereto.

EXAMPLE I

Preparation of a Genomic Library

The following example illustrates the preparation of a Bacillus genomic library.

Genomic DNA from Bacillus cells is prepared as taught in Current Protocols In Molecular Biology vol. 1, edited by Ausubel et al., John Wiley & Sons, Inc. 1987, chapter 2. 4.1. Generally, Bacillus cells from a saturated liquid culture are lysed and the proteins removed by digestion with proteinase K. Cell wall debris, polysaccharides, and remaining proteins are removed by selective precipitation with CTAB, and high molecular weight genomic DNA is recovered from the resulting supernatant by isopropanol precipitation. If exceptionally clean genomic DNA is desired, an additional step of purifying the Bacillus genomic DNA on a cesium chloride gradient is added.

After obtaining purified genomic DNA, the DNA is subjected to Sau3A digestion. Sau3A recognizes the 4 base pair site GATC and generates fragments compatible with several convenient phage lambda and cosmid vectors. The DNA is subjected to partial digestion to increase the chance of obtaining random fragments.

The partially digested Bacillus genomic DNA is subjected to size fractionation on a 1% agarose gel prior to cloning into a vector. Alternatively, size fractionation on a sucrose gradient can be used. The genomic DNA obtained from the size fractionation step is purified away from the agarose and ligated into a cloning vector appropriate for use in a host cell and transformed into the host cell.

EXAMPLE II

Detection of Gram-positive Microorganisms

The following example describes the detection of gram-positive microorganism CP1. The same procedures can be used to detect CP2 and CP3.

DNA derived from a gram-positive microorganism is prepared according to the methods disclosed in Current Protocols in Molecular Biology, Chap. 2 or 3. The nucleic acid is subjected to hybridization and/or PCR amplification with a probe or primer derived from CP1. A preferred probe comprises the nucleic acid section containing the conserved motif GXCWAF.

The nucleic acid probe is labeled by combining 50 pmol of the nucleic acid and 250 mCi of [gamma $^{32}$P] adenosine triphosphate (Amersham, Chicago Ill.) and T4 polynucleotide kinase (DuPont NEN®, Boston Mass.). The labeled probe is purified with Sephadex G-25 super fine resin column (Pharmacia). A portion containing $10^7$ counts per minute of each is used in a typical membrane based hybridization analysis of nucleic acid sample of either genomic or cDNA origin.

The DNA sample which has been subjected to restriction endonuclease digestion is fractionated on a 0.7 percent agarose gel and transferred to nylon membranes (Nytran Plus, Schleicher & Schuell, Durham N.H.). Hybridization is carried out for 16 hours at 40 degrees C. To remove nonspecific signals, blots are sequentially washed at room temperature under increasingly stringent conditions up to 0.1×saline sodium citrate and 0.5% sodium dodecyl sulfate. The blots are exposed to film for several hours, the film developed and hybridization patterns are compared visually to detect polynucleotide homologs of B.subtilis CP1. The homologs are subjected to confirmatory nucleic acid sequencing. Methods for nucleic acid sequencing are well known in the art. Conventional enzymatic methods employ DNA polymerase Klenow fragment, SEQUENASE® (US Biochemical Corp, Cleveland, Ohio) or Taq polymerase to extend DNA chains from an oligonucleotide primer annealed to the DNA template of interest.

Various other examples and modifications of the foregoing description and examples will be apparent to a person skilled in the art after reading the disclosure without departing from the spirit and scope of the invention, and it is intended that all such examples or odifications be included within the scope of the appended claims. All publications and patents referenced herein are hereby incorporated by reference in their entirety.

What is claimed is:

1. A *Bacillus subtilis* having a mutation or deletion of part or all of the gene encoding cysteine protease-1 CP1, wherein said gene encodes the amino acid sequence set forth in SEQ ID NO:2, and said mutation or deletion results in the inactivation of the CP1 proteolytic activity.

2. The *Bacillus subtilis* of claim 1, wherein said *Bacillus subtilis* is capable of expressing a heterologous protein.

3. The *Bacillus subtilis* of claim 1, wherein said heterologous protein is selected from the group consisting of hormones, enzymes, growth factors, and cytokines.

4. The *Bacillus subtilis* of claim 3 wherein said heterologous protein is an enzyme.

5. The *Bacillus subtilis* of claim 4 wherein said enzyme is selected from the group consisting of proteases, carbohydrases, lipases, isomerases, racemases, epimerases, tautomerases, mutases, transferases, kinases and phosphatases.

6. A method for the production of a heterologous protein in a transformed *Bacillus subtilis* host cell comprising the steps of:
  (a) obtaining a *Bacillus subtilis* host cell comprising a nucleic acid encoding said heterciogous protein wherein said host cell contains a mutation or deletion in the gene encoding *B subtilis* cysteine protease-1, wherein said gene encoding cysteine protease-1 encodes the amino acid sequence set forth in SEQ ID NO:2, and said mutation or deletion results in the inactivation of the cysteine protease-1 proteolytic activity: and
  (b) growing said *Bacillus Subtilis* host cell under conditions suitable for the expression of said heterologous protein.

7. The method of claim 6, wherein said gene encoding cysteine protease-1 comprises the nucleic acid sequence set forth in SEQ ID NO:1.

* * * * *

SEQUENCE LISTING

<160> NUMBER OF SEQ ID NOS: 7

<210> SEQ ID NO 1
<211> LENGTH: 945
<212> TYPE: DNA
<213> ORGANISM: Bacillius subtilis

<400> SEQUENCE: 1

```
atgacgactg aaccgttatt tttcaagcct gttttcaaag aaagaatttg gggcgggacc    60
gctttagctg attttggcta taccattccg tcacaacgaa caggggagtg ctgggctttt   120
gccgcgcatc aaaatggtca aagcgttgtt caaaacggaa tgtataaggg gttcacgctc   180
agcgaattat gggaacatca cagacattta ttcggacagc ttgaagggga ccgtttccct   240
ctgcttacaa aaatattaga tgctgaccag gacttatctg ttcaggtgca tccgaatgat   300
gaatatgcca acatacatga aaacggtgag cttggaaaaa cagaatgctg gtacattatt   360
gattgccaaa aagatgccga gattatttat ggccacaatg caacaacaaa ggaagaacta   420
actaccatga tagagcgtgg agaatgggat gagctcttgc gccgtgtaaa ggtaaagccg   480
ggggattttt tctatgtgcc aagcggtact gttcatgcga ttggaaaagg aattcttgct   540
ttggagacgc agcagaactc agacacaacc tacagattat atgattatga ccgaaaagat   600
gcagaaggca agctgcgcga gcttcatctg aaaaagagca ttgaagtgat agaggtcccg   660
```

```
tctattccag aacggcatac agttcaccat gaacaaattg aggatttgct tacaacgaca      720
ttgattgaat gcgcttactt ttcggtgggg aaatggaact tatcaggatc agcaagctta      780
aagcagcaaa aaccattcct tcttatcagt gtgattgaag gggagggccg tatgatctct      840
ggtgagtatg tctatccttt caaaaaagga gatcatatgt tgctgcctta cggtcttgga      900
gaatttaaac tcgaaggata tgcagaatgt atcgtctccc atctg                      945
```

<210> SEQ ID NO 2
<211> LENGTH: 315
<212> TYPE: PRT
<213> ORGANISM: Bacillus subtilis

<400> SEQUENCE: 2

```
Met Thr Thr Glu Pro Leu Phe Phe Lys Pro Val Phe Lys Glu Arg Ile
  1               5                  10                  15

Trp Gly Gly Thr Ala Leu Ala Asp Phe Gly Tyr Thr Ile Pro Ser Gln
             20                  25                  30

Arg Thr Gly Glu Cys Trp Ala Phe Ala Ala His Gln Asn Gly Gln Ser
         35                  40                  45

Val Val Gln Asn Gly Met Tyr Lys Gly Phe Thr Leu Ser Glu Leu Trp
     50                  55                  60

Glu His His Arg His Leu Phe Gly Gln Leu Glu Gly Asp Arg Phe Pro
 65                  70                  75                  80

Leu Leu Thr Lys Ile Leu Asp Ala Asp Gln Asp Leu Ser Val Gln Val
                 85                  90                  95

His Pro Asn Asp Glu Tyr Ala Asn Ile His Glu Asn Gly Glu Leu Gly
            100                 105                 110

Lys Thr Glu Cys Trp Tyr Ile Ile Asp Cys Gln Lys Asp Ala Glu Ile
        115                 120                 125

Ile Tyr Gly His Asn Ala Thr Thr Lys Glu Glu Leu Thr Thr Met Ile
    130                 135                 140

Glu Arg Gly Glu Trp Asp Glu Leu Leu Arg Arg Val Lys Val Lys Pro
145                 150                 155                 160

Gly Asp Phe Phe Tyr Val Pro Ser Gly Thr Val His Ala Ile Gly Lys
                165                 170                 175

Gly Ile Leu Ala Leu Glu Thr Gln Gln Asn Ser Asp Thr Thr Tyr Arg
            180                 185                 190

Leu Tyr Asp Tyr Asp Arg Lys Asp Ala Glu Gly Lys Leu Arg Glu Leu
        195                 200                 205

His Leu Lys Lys Ser Ile Glu Val Ile Glu Val Pro Ser Ile Pro Glu
    210                 215                 220

Arg His Thr Val His His Glu Gln Ile Glu Asp Leu Leu Thr Thr Thr
225                 230                 235                 240

Leu Ile Glu Cys Ala Tyr Phe Ser Val Gly Lys Trp Asn Leu Ser Gly
                245                 250                 255

Ser Ala Ser Leu Lys Gln Gln Lys Pro Phe Leu Ile Ser Val Ile
            260                 265                 270

Glu Gly Glu Gly Arg Met Ile Ser Gly Glu Tyr Val Tyr Pro Phe Lys
        275                 280                 285

Lys Gly Asp His Met Leu Leu Pro Tyr Gly Leu Gly Glu Phe Lys Leu
    290                 295                 300

Glu Gly Tyr Ala Glu Cys Ile Val Ser His Leu
305                 310                 315
```

<210> SEQ ID NO 3
<211> LENGTH: 220
<212> TYPE: PRT
<213> ORGANISM: Bacillus subtilis

<400> SEQUENCE: 3

```
Val Leu Asn Asp Gly Asp Val Asn Ile Pro Glu Tyr Val Asp Trp Arg
 1               5                  10                  15

Gln Lys Gly Ala Val Thr Pro Val Lys Asn Gln Gly Ser Cys Gly Ser
            20                  25                  30

Cys Trp Ala Phe Ser Ala Val Val Thr Ile Glu Gly Ile Ile Lys Ile
        35                  40                  45

Arg Thr Gly Asn Leu Asn Glu Tyr Ser Glu Gln Glu Leu Leu Asp Cys
    50                  55                  60

Asp Arg Arg Ser Tyr Gly Cys Asn Gly Gly Tyr Pro Trp Ser Ala Leu
65                  70                  75                  80

Gln Leu Val Ala Gln Tyr Gly Ile His Tyr Arg Asn Thr Tyr Pro Tyr
                85                  90                  95

Glu Gly Val Gln Arg Tyr Cys Arg Ser Arg Glu Lys Gly Pro Tyr Ala
            100                 105                 110

Ala Lys Thr Asp Gly Val Arg Gln Val Gln Pro Tyr Asn Glu Gly Ala
        115                 120                 125

Leu Leu Tyr Ser Ile Ala Asn Gln Pro Val Ser Val Leu Glu Ala
    130                 135                 140

Ala Gly Lys Asp Phe Gln Leu Tyr Arg Gly Gly Ile Phe Val Gly Pro
145                 150                 155                 160

Cys Gly Asn Lys Val Asp His Ala Val Ala Ala Val Gly Tyr Gly Pro
                165                 170                 175

Asn Tyr Ile Leu Ile Lys Asn Ser Trp Gly Thr Gly Trp Gly Glu Asn
            180                 185                 190

Gly Tyr Ile Arg Ile Lys Arg Gly Thr Gly Asn Ser Tyr Gly Val Cys
        195                 200                 205

Gly Leu Tyr Thr Ser Ser Phe Tyr Pro Val Lys Asn
    210                 215                 220
```

<210> SEQ ID NO 4
<211> LENGTH: 948
<212> TYPE: DNA
<213> ORGANISM: Bacillus subtilis

<400> SEQUENCE: 4

```
atgacgcaat caccgatttt tctaacgcct gtgtttaaag aaaaaatctg gggcggaacc      60
gctttacgag atagatttgg atacagtatt ccttcagaat caacggggga atgctgggcc     120
atttccgctc atccaaaagg accgagcact gttgcaaatg gcccgtataa aggaaagaca     180
ttgatcgagc tttgggaaga gcaccgtgaa gtattcggcg cgtagaggg  ggatcggttt     240 ccgcttctga caaagctgct ggatgtgaag gaagatacgt caattaaagt tcaccctgat     300
gattactatg ccggagaaaa cgaagaggga gaactcggca agacggaatg ctggtacatt     360
atcgactgta aggaaaacgc agaaatcatt tacgggcata cggcccgctc aaaaaccgaa     420
cttgtcacaa tgatcaacag cggtgactgg gagggcctgc tgcgaagaat caaaattaaa     480
ccgggtgatt tctattatgt gccgagcgga acgctgcacg cattgtgcaa ggggccctt      540 gttttagaga ctcagcaaaa ttcagatgcc acataccggg tgtacgatta tgaccgtctt     600
gatagcaacg gaagtccgag agagcttcat tttgccaaag cggtcaatgc cgccacggtt     660
```

```
ccccatgtgg acgggtatat agatgaatcg acagaatcaa gaaaaggaat aaccattaaa    720
acatttgtcc aagggaata ttttcggtt tataaatggg acatcaatgg cgaagctgaa    780
atggctcagg atgaatcctt tctgatttgc agcgtgatag aaggaagcgg tttgctcaag    840
tatgaggaca aacatgtcc gctcaaaaaa ggtgatcact ttatttttgcc ggctcaaatg    900 cccgatttta cgataaaagg aacttgtacc cttatcgtgt ctcatatt              948
```

<210> SEQ ID NO 5
<211> LENGTH: 316
<212> TYPE: PRT
<213> ORGANISM: Bacillus subtilis

<400> SEQUENCE: 5

```
Met Thr Gln Ser Pro Ile Phe Leu Thr Pro Val Phe Lys Glu Lys Ile
 1               5                  10                  15

Trp Gly Gly Thr Ala Leu Arg Asp Arg Phe Gly Tyr Ser Ile Pro Ser
            20                  25                  30

Glu Ser Thr Gly Glu Cys Trp Ala Ile Ser Ala His Pro Lys Gly Pro
        35                  40                  45

Ser Thr Val Ala Asn Gly Pro Tyr Lys Gly Lys Thr Leu Ile Glu Leu
    50                  55                  60

Trp Glu Glu His Arg Glu Val Phe Gly Gly Val Glu Gly Asp Arg Phe
65                  70                  75                  80

Pro Leu Leu Thr Lys Leu Leu Asp Val Lys Glu Asp Thr Ser Ile Lys
                85                  90                  95

Val His Pro Asp Asp Tyr Tyr Ala Gly Glu Asn Glu Glu Gly Glu Leu
            100                 105                 110

Gly Lys Thr Glu Cys Trp Tyr Ile Ile Asp Cys Lys Glu Asn Ala Glu
        115                 120                 125

Ile Ile Tyr Gly His Thr Ala Arg Ser Lys Thr Glu Leu Val Thr Met
    130                 135                 140

Ile Asn Ser Gly Asp Trp Glu Gly Leu Leu Arg Arg Ile Lys Ile Lys
145                 150                 155                 160

Pro Gly Asp Phe Tyr Tyr Val Pro Ser Gly Thr Leu His Ala Leu Cys
                165                 170                 175

Lys Gly Ala Leu Val Leu Glu Thr Gln Gln Asn Ser Asp Ala Thr Tyr
            180                 185                 190

Arg Val Tyr Asp Tyr Asp Arg Leu Asp Ser Asn Gly Ser Pro Arg Glu
        195                 200                 205

Leu His Phe Ala Lys Ala Val Asn Ala Ala Thr Val Pro His Val Asp
    210                 215                 220

Gly Tyr Ile Asp Glu Ser Thr Glu Ser Arg Lys Gly Ile Thr Ile Lys
225                 230                 235                 240

Thr Phe Val Gln Gly Glu Tyr Phe Ser Val Tyr Lys Trp Asp Ile Asn
                245                 250                 255

Gly Glu Ala Glu Met Ala Gln Asp Glu Ser Phe Leu Ile Cys Ser Val
            260                 265                 270

Ile Glu Gly Ser Gly Leu Leu Lys Tyr Glu Asp Lys Thr Cys Pro Leu
        275                 280                 285

Lys Lys Gly Asp His Phe Ile Leu Pro Ala Gln Met Pro Asp Phe Thr
    290                 295                 300

Ile Lys Gly Thr Cys Thr Leu Ile Val Ser His Ile
305                 310                 315
```

<210> SEQ ID NO 6
<211> LENGTH: 945
<212> TYPE: DNA
<213> ORGANISM: Bacillus subtilis

<400> SEQUENCE: 6

```
atgacgcatc cattattttt agagcctgtc tttaaagaaa gactatgggg agggacgaag      60
cttcgtgacg cttttggcta cgcaataccc tcacaaaaaa caggtgagtg ctgggccgtt     120
tctgcacatg cccatggctc gtcgtctgta aaaaatggcc cgctggcagg aaagacactt     180
gatcaagtat ggaaagatca tccagagata ttcgggtttc cggatggtaa ggtgtttccg     240
ctgctggtaa agctgctgga cgccaatatg gatctctccg tgcaagtcca tcctgatgat     300
gattatgcaa aactgcacga aaatggcgac cttggtaaaa cggagtgctg gtatatcatt     360
gattgcaaag atgacgccga actaattttg ggacatcatg caagcacaaa ggaagagttc     420
aaacaacgaa tagaaagcgg tgattggaac gggctgctga ggcgaatcaa aatcaagcca     480
ggagatttct tttatgtgcc aagcggtaca ctccatgctt tatgtaaggg aacccttgtc     540
cttgaaatcc agcaaaactc tgatacaaca tatcgcgtat acgattatga ccgctgtaat     600
gaccagggcc aaaaaagaac tcttcatata gaaaaagcca tggaagtcat aacgataccg     660
catatcgata agtgcatac accggaagta aaagaagttg gtaacgctga gatcattgtt     720
tatgtgcaat cagattattt ctcagtgtac aaatggaaga ttagcggccg agctgctttt     780
ccttcatatc aaacctattt gctggggagt gttctgagcg gatcaggacg aatcataaat     840
aatggtattc agtatgaatg caatgcaggc tcacacttta ttctgcctgc gcattttgga     900
gaatttacaa tagaaggaac atgtgaattc atgatatctc atcct                     945
```

<210> SEQ ID NO 7
<211> LENGTH: 315
<212> TYPE: PRT
<213> ORGANISM: Bacillus subtilis

<400> SEQUENCE: 7

```
Met Thr His Pro Leu Phe Leu Glu Pro Val Phe Lys Glu Arg Leu Trp
  1               5                  10                  15

Gly Gly Thr Lys Leu Arg Asp Ala Phe Gly Tyr Ala Ile Pro Ser Gln
             20                  25                  30

Lys Thr Gly Glu Cys Trp Ala Val Ser Ala His Ala His Gly Ser Ser
         35                  40                  45

Ser Val Lys Asn Gly Pro Leu Ala Gly Lys Thr Leu Asp Gln Val Trp
     50                  55                  60

Lys Asp His Pro Glu Ile Phe Gly Phe Pro Asp Gly Lys Val Phe Pro
 65                  70                  75                  80

Leu Leu Val Lys Leu Leu Asp Ala Asn Met Asp Leu Ser Val Gln Val
                 85                  90                  95

His Pro Asp Asp Asp Tyr Ala Lys Leu His Glu Asn Gly Asp Leu Gly
            100                 105                 110

Lys Thr Glu Cys Trp Tyr Ile Ile Asp Cys Lys Asp Asp Ala Glu Leu
        115                 120                 125

Ile Leu Gly His His Ala Ser Thr Lys Glu Glu Phe Lys Gln Arg Ile
    130                 135                 140

Glu Ser Gly Asp Trp Asn Gly Leu Leu Arg Arg Ile Lys Ile Lys Pro
145                 150                 155                 160

Gly Asp Phe Phe Tyr Val Pro Ser Gly Thr Leu His Ala Leu Cys Lys
                165                 170                 175
```

-continued

```
Gly Thr Leu Val Leu Glu Ile Gln Gln Asn Ser Asp Thr Thr Tyr Arg
            180                 185                 190

Val Tyr Asp Tyr Asp Arg Cys Asn Asp Gln Gly Gln Lys Arg Thr Leu
        195                 200                 205

His Ile Glu Lys Ala Met Glu Val Ile Thr Ile Pro His Ile Asp Lys
    210                 215                 220

Val His Thr Pro Glu Val Lys Glu Val Gly Asn Ala Glu Ile Ile Val
225                 230                 235                 240

Tyr Val Gln Ser Asp Tyr Phe Ser Val Tyr Lys Trp Lys Ile Ser Gly
            245                 250                 255

Arg Ala Ala Phe Pro Ser Tyr Gln Thr Tyr Leu Leu Gly Ser Val Leu
            260                 265                 270

Ser Gly Ser Gly Arg Ile Ile Asn Asn Gly Ile Gln Tyr Glu Cys Asn
        275                 280                 285

Ala Gly Ser His Phe Ile Leu Pro Ala His Phe Gly Glu Phe Thr Ile
        290                 295                 300

Glu Gly Thr Cys Glu Phe Met Ile Ser His Pro
305                 310                 315
```